(12) United States Patent
Nauche et al.

(10) Patent No.: US 10,194,795 B2
(45) Date of Patent: Feb. 5, 2019

(54) APPARATUS AND METHOD FOR SCREENING FOR DEFECTS IN THE SIGHT AND FOR MEASURING THE VISUAL ACUITY OF A USER

(71) Applicant: ESSILOR INTERNATIONAL (COMPAGNIE GENERALE D'OPTIQUE), Charenton-le-pont (FR)

(72) Inventors: Michel Nauche, Charenton-le-pont (FR); Stephane Boutinon, Charenton-le-pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 198 days.

(21) Appl. No.: 15/105,173

(22) PCT Filed: Dec. 12, 2014

(86) PCT No.: PCT/FR2014/053316
§ 371 (c)(1),
(2) Date: Jun. 16, 2016

(87) PCT Pub. No.: WO2015/092233
PCT Pub. Date: Jun. 25, 2015

(65) Prior Publication Data
US 2017/0000328 A1    Jan. 5, 2017

(30) Foreign Application Priority Data

Dec. 17, 2013 (FR) ...................................... 13 62840

(51) Int. Cl.
*A61B 3/032*     (2006.01)
*A61B 3/00*      (2006.01)
(Continued)

(52) U.S. Cl.
CPC ............ *A61B 3/032* (2013.01); *A61B 3/0033* (2013.01); *A61B 3/0041* (2013.01); *A61B 3/12* (2013.01); *A61B 5/741* (2013.01)

(58) Field of Classification Search
CPC ....... A61B 3/032; A61B 3/0025; A61B 3/028; A61B 3/0033; A61B 3/0041; A61B 3/02; (Continued)

(56) References Cited

U.S. PATENT DOCUMENTS 4,597,651 A * 7/1986 Capo-Gual ............ A61B 3/024
                                                       351/239
2011/0025977 A1   2/2011 Yoo et al.
(Continued)

FOREIGN PATENT DOCUMENTS

CN    102573610 A    7/2012
EP    0 102 887 A    3/1984
(Continued)

OTHER PUBLICATIONS

EP 2 454 988 English machine translation.*
International Search Report, dated Mar. 18, 2015, from corresponding PCT application.

*Primary Examiner* — Thomas K Pham
*Assistant Examiner* — Sharrief Broome
(74) *Attorney, Agent, or Firm* — Young & Thompson (57) ABSTRACT

A binocular optoelectronic apparatus for screening defects in the sight and for measuring the visual acuity of a user, includes a casing having a right-hand first aperture and a left-hand first aperture, which apertures are intended to be placed facing the right eye and the left eye of a user facing in a first gaze direction, respectively. This apparatus includes: a touchscreen placed so that a first zone of the touchscreen is located in the interior of the casing and a second zone of the touchscreen is accessible from the exterior of the casing; electronic elements suitable for dis-
(Continued)

playing a plurality of optotypes on a first portion of the first zone; and an optical system configured to form a right-hand first image of the first portion of the first zone in the direction of the first right-hand aperture at a first vision distance along a first optical path.

20 Claims, 3 Drawing Sheets (51) Int. Cl.
*A61B 3/12* (2006.01)
*A61B 5/00* (2006.01)

(58) Field of Classification Search
CPC ....... A61B 3/0091; A61B 3/022; A61B 3/024; A61B 3/036; A61B 3/08; A61B 3/0285; A61B 3/09; A61B 3/1015; A61B 3/103; A61B 3/0058; A61B 3/0075; A61B 3/00
See application file for complete search history.

(56) References Cited

U.S. PATENT DOCUMENTS

| | | | | |
|---|---|---|---|---|
| 2011/0027766 | A1* | 2/2011 | Yoo | A61H 5/00 434/262 |
| 2012/0075586 | A1* | 3/2012 | Kirschen | A61B 3/028 351/239 |
| 2013/0128229 | A1 | 5/2013 | Huang | |

FOREIGN PATENT DOCUMENTS

| | | | | |
|---|---|---|---|---|
| EP | 2 454 988 | * | 5/2012 | ............. A61B 3/024 |
| EP | 2 454 988 A1 | | 5/2012 | |

* cited by examiner

APPARATUS AND METHOD FOR SCREENING FOR DEFECTS IN THE SIGHT AND FOR MEASURING THE VISUAL ACUITY OF A USER

TECHNICAL FIELD TO WHICH THE INVENTION RELATES

Generally, the present invention relates to the field of apparatuses and methods for the optical examination of the eyes.

It more particularly relates to an apparatus and method for screening for defects in the sight of a person and/or for measuring visual acuity.

This type of apparatus is intended to be used in any situation in which it is necessary to screen for visual defects. In particular, such an apparatus is intended to be used to screen for visual defects in the context of workplace health, a driver's license examination, self-testing in a pharmacy, during the sale of a pair of reading spectacles for example.

This type of apparatus is also intended to be used in the context of visual screening and/or of measurement of visual acuity by an optician or a hearing specialist in a shop.

The invention in particular relates to an apparatus and method of the subjective measurement type, i.e. a test apparatus requiring the active participation of the patient.

TECHNOLOGICAL BACKGROUND

A self-test apparatus for examining the sight of the two eyes of a patient, and for self-screening for visual defects without intervention of an operator is especially known from document EP0102887_B1. The apparatus includes an optical system that allows test images borne by a roll of film to be viewed, said test images being presented along three distinct optical channels, corresponding to near-vision, far-vision and intermediate-vision distances, respectively. Advantageously, the self-test apparatus includes a loudspeaker circuit and a recording circuit that are coupled and/or synchronized with the rotation of the roll of film, in order to give instructions and/or ask questions to the patient and to record the responses of the patient depending on the viewed test images.

An apparatus for screening for visual defects is also known, under the trade name Ergovision by Essilor, which allows optical tests or optotypes to be presented at various vision distances. The person tested passes from far vision, to intermediate vision then to near vision simply by lowering his gaze. A voice-synthesizing device allows the sequence of a series of tests to be automatically controlled. The patient may respond to the questions via buttons of a remote control.

The test images or optotypes used in these screening apparatuses, for example to measure visual acuity or to screen for hypermetropia, are in general alphanumeric characters arranged analogously to a Monoyer scale of eye tests. These tests allow clear instructions to be given such as, for example: "read line No. X", and allow easily understandable responses to be recorded.

Nevertheless, alphanumeric-type test images are not usable with illiterate people. Furthermore, visual acuity measurement bias may arise from memorization of series of letters or numbers by the patient or from a tendency of the patient to guess more than view the displayed alphanumeric characters.

However, the screening of visual defects must now conform with the standard ISO8596, which not only defines the optotype presentation distances but also the form of the optotypes.

According to this standard, the optotypes must be presented at a distance corresponding to a far vision larger than 4 meters. The near-vision distance is not standardized but a distance range comprised between 33 and 50 cm is commonly cited.

In addition, according to the standard ISO8596, visual screening tests must be based on a Landolt scale, which includes a series of identical optotypes, which are called Landolt rings, taking the form of circles comprising an aperture or break. The diameter of the circle varies depending on the tested visual acuity. The orientation of the aperture of the circle varies in various directions that may be: 0, +45 degrees, +90 degrees, +135 degrees, +180 degrees, +225 degrees, +270 degrees and +315 degrees relative to a vertical line.

The Landolt scale has the advantage of being able to be used by illiterate people. In addition, it is difficult for a patient to guess a lighter or darker zone corresponding to the orientation of the aperture of a Landolt ring. In theory, the Landolt scale allows acuity measurements not bringing into play the memorization of the morphology of a letter. In practice, for a given acuity to be tested, i.e. for a Landolt ring of determined diameter, the ring is presented with a random orientation a certain number of times so as to make it possible to determine whether the visual performance is achieved or not.

However, the oral response of a patient to indicate the orientation of a Landolt ring raises problems of reliability. Specifically, though the indications top and bottom are widely assimilated by all of the population, the notion of right and left may be subject to confusion. For the other directions, such as +45 degrees, +135 degrees, +225 degrees and +315 degrees, it is in general very difficult to be sure of the relevance of the response. This use of a Landolt scale may lead to an incorrect response from the user, even though this user has visually detected the correct orientation of the ring.

It is therefore necessary to be able to record the responses of the patient to a test based on a Landolt scale in a trustworthy way that does not introduce false positives.

Some known apparatuses presenting Landolt rings use a joystick by way of user interface. If the use of such an accessory is familiar to a population accustomed to videogames, it is not completely spontaneous for a novice.

In general, the visual screening apparatuses of the prior art do not allow the Landolt-scale test images indicated in standard ISO8596 to be used reliably.

One of the aims of the invention is to provide an apparatus and method for screening for defects in the sight of a person allowing, in a compact volume, optotypes, in particular taking the form of Landolt rings, to be presented at two very different vision distances and a reliable response of the tested person to be recorded.

SUBJECT OF THE INVENTION

In order to remedy the aforementioned drawbacks of the prior art, the present invention provides a bi-ocular optoelectronic apparatus for screening for defects in the sight of and for measuring the visual acuity of a user, the bi-ocular optoelectronic apparatus including a housing having a first right aperture and a first left aperture, which apertures are respectively intended to be placed facing the right eye and left eye of the user facing in a first direction of sight.

More particularly, according to the invention a bi-ocular optoelectronic apparatus for screening for visual defects and for measuring visual acuity is proposed, including:
- a touchscreen comprising a first zone and a second zone that are spatially separate, the touchscreen being placed in the bi-ocular optoelectronic apparatus so that the first zone of the touchscreen is in the interior of the housing and so that the second zone of the touchscreen is accessible from the exterior of the housing;
- electronic means suitable for displaying a plurality of optotypes in a first portion of the first zone of the touchscreen, internal to the housing;
- an optical system placed in the interior of the housing, the optical system being configured to form a first right image of the first portion of the first zone of the touchscreen in the direction of the first right aperture at a first vision distance following a first optical path, and the optical system being configured to form a first left image of the first portion of the first zone of the touchscreen in the direction of the first left aperture at said first vision distance following a second optical path.

The screening apparatus thus allows, using a single screen, optotypes to be displayed in a controlled luminous environment in the interior of a housing and general information, such as a user manual, an invitation to start or continue the visual screening test, to be presented to the user. This apparatus makes it possible to modify the displayed optotypes without moving the optomechanical component. The screen of the screening apparatus integrates both the functions of light source and of physical support of optotypes in limitless number.

According to one particular and advantageous embodiment, the second zone of the touchscreen is configured to record touch interactions of the user and the bi-ocular optoelectronic apparatus for screening for visual defects and for measuring visual acuity furthermore includes electronic processing means suitable for modifying the display of said pto types in the first portion of the first zone of the screen depending on the recorded touch interactions and/or to record a response of the user to a viewed first right image and/or to a viewed first left image depending on said recorded touch interactions.

Advantageously, the bi-ocular optoelectronic apparatus for screening for visual defects and for measuring visual acuity furthermore includes:
- a second right aperture and a second left aperture, which apertures are respectively intended to be placed facing the right eye and the left eye of the user facing in a second direction of sight;
- electronic means suitable for displaying a plurality of optotypes in a second portion of the first zone of the touchscreen, internal to the housing, said first portion and second portion of the first zone of the touchscreen being spatially separate; and
- the optical system being configured to form a second right image of the second portion of the first zone of the touchscreen in the direction of the second right aperture at a second vision distance following a third optical path, and the optical system being configured to form a second left image of the second portion of the first zone of the touchscreen in the direction of the second left aperture at said second vision distance following a fourth optical path.

According to one particular and advantageous embodiment, the bi-ocular optoelectronic apparatus for screening for visual defects and for measuring visual acuity furthermore includes:
- a third right aperture and a third left aperture, which apertures are respectively intended to be placed facing the right eye and the left eye of the user facing in a third direction of sight; and
- the optical system being configured to form a third right image of the third portion of the first zone of the touchscreen in the direction of the third right aperture at a third vision distance following a fifth optical path, and the optical system being configured to form a third left image of the third portion of the first zone of the touchscreen in the direction of the third left aperture at said third vision distance following a sixth optical path.

The following are other nonlimiting advantageous features of a bi-ocular optoelectronic apparatus for screening for visual defects and for measuring visual acuity according to the invention:
- the touchscreen is placed in the bi-ocular optoelectronic apparatus so as to have an external third zone intended to serve as an operator interface, said external third zone being spatially separate from said first zone and second zone of the touchscreen;
- the plurality of optotypes includes a Landolt ring having a determined orientation and diameter and the processing means are suitable for indicating the orientation or for modifying the orientation and/or the diameter of the Landolt ring by interaction of the user via the external second zone of the touchscreen;
- the plurality of optotypes includes an alphanumeric character having a determined size and the processing means are suitable for designating an alphanumeric character from a set of alphanumeric characters or for modifying the displayed alphanumeric character and/or the size of the displayed alphanumeric character by interaction of the user via the external second zone of the touchscreen;
- the first zone of the touchscreen, internal to the housing, is suitable for forming an illuminating means suitable for illuminating an optotype for measuring reserve accommodation or for illuminating the right eye and/or left eye of the user, preferably during the display of an optotype;
- the touchscreen is removable from the housing of the apparatus.

According to one particular and advantageous embodiment, the bi-ocular optoelectronic apparatus for screening for visual defects and for measuring visual acuity furthermore includes:
- electronic processing means suitable for modifying the display of the plurality of optotypes in the first zone of the touchscreen depending on interactions of the user, which interactions are recorded via the external second zone of the touchscreen;
- means for recording an interaction of the user via the external second zone of the touchscreen and in which the electronic processing means are suitable for deducing from this recording a measurement of the visual acuity of the right eye and/or of the left eye for the first vision distance, for the second vision distance and/or for the third vision distance, respectively, the first vision distance preferably corresponding to a near-vision distance smaller than or equal to 50 cm, the second vision distance preferably corresponding to a far-vision distance larger than or equal to 4 meters and the third vision distance preferably corresponding to an intermediate-vision distance comprised between 50 cm and 3 m;

obturating means suitable for selectively obturating a first, second and/or third right aperture and/or a first, second and/or third left aperture, said obturating means for example comprising spatially selective means for displaying on the touchscreen;

means for modifying the luminance and/or contrast of the images displayed in the first zone of the touchscreen;

means for measuring the punctum proximum of accommodation of the user;

the first zone of the touchscreen, internal to the housing, is suitable for forming an illuminating means suitable for illuminating an optotype for measuring the punctum proximum of accommodation;

the touchscreen is removable from the housing of the apparatus.

The invention also provides a method for screening for defects in the sight of and for measuring the visual acuity of a user, the method implementing a bi-ocular optoelectronic apparatus as claimed in one of claims 1 to 14 and comprising the following steps:

a. displaying a plurality of optotypes in the first zone of the touchscreen, said plurality of optotypes comprising at least one Landolt ring, having a diameter and an aperture of predetermined orientation;

b. modifying the diameter and/or a visually detected indication of the orientation of the aperture of the Landolt ring by interaction via the second zone of the touchscreen;

c. validating, via the second zone of the touchscreen, a diameter and/or a visually detected indication of the orientation of the Landolt ring, this validation being by the user.

Lastly, the invention provides a method for screening for defects in the sight of and for measuring the visual acuity of a user, the method implementing a bi-ocular optoelectronic apparatus as claimed in one of claims 1 to 14 and comprising the following steps:

a. displaying a plurality of optotypes in the first zone of the touchscreen, said plurality of optotypes comprising at least one alphanumeric character, having a predetermined size;

b. modifying the displayed alphanumeric character, the size of the displayed alphanumeric character and/or an indication of the alphanumeric character by interaction via the second zone of the touchscreen;

c. validating, via the second zone of the touchscreen, a size and/or an indication of the displayed alphanumeric character, this validation being by the user.

DETAILED DESCRIPTION OF ONE EXEMPLARY EMBODIMENT

The description which follows with regard to the appended drawings given by way of nonlimiting examples will clearly elucidate the essence of the invention and the manner in which it may be carried out.

DEVICE

Figure 1:
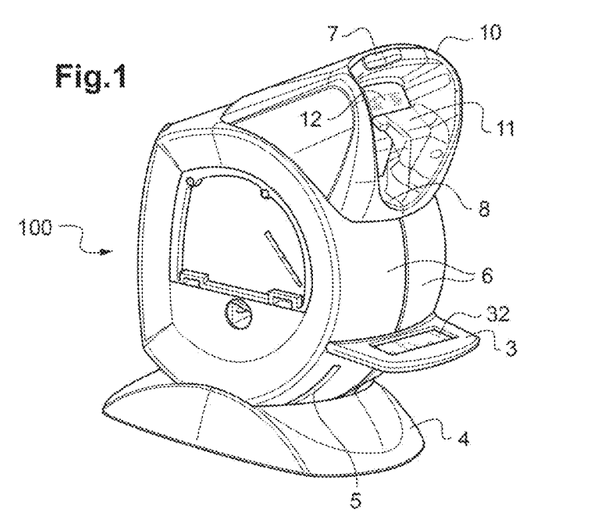
FIG. 1 schematically shows an external perspective view of a visual screening apparatus according to one embodiment of the invention.
Figure 2:
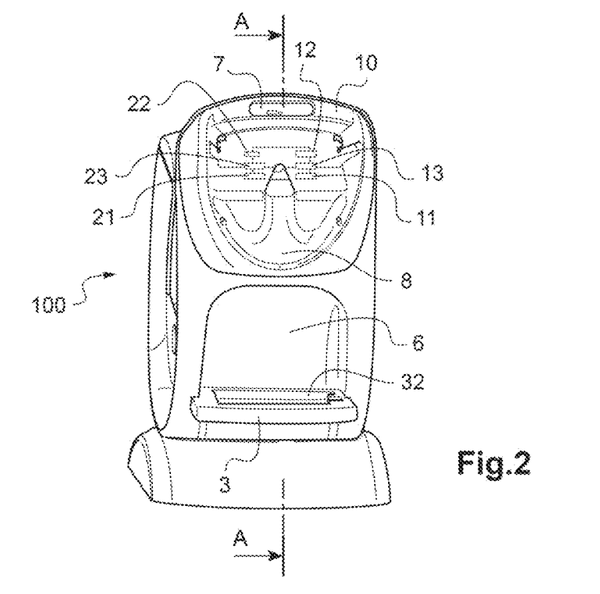
FIG. 2 shows a view from the user-side of a visual screening apparatus according to one variant of FIG. 1.

FIGS. 1-2 show external views of a visual screening apparatus 100 according to two variants of one embodiment of the invention.

The visual screening apparatus 100 illustrated in FIGS. 1-2 takes the form of a compact apparatus that can be placed on a table. The visual screening apparatus 100 includes a stand 4 and a housing 10, composed of one or more elements, that surrounds the internal optoelectronic system of the apparatus. The housing 10 serves to optically isolate the internal optoelectronic system from ambient light.

Particularly advantageously, the apparatus includes a zone 7 against which the forehead may rest and/or a chin rest 8 in order to maintain the head of the user in a fixed position, whatever the direction of the axis of sight of the gaze.

Optionally, the apparatus 100 comprises a guiding rail 5 that allows the housing 10 to be inclined relative to the stand 4, so as to adapt the apparatus to the size of the user for comfort in the tests.

FIG. 2 shows the side of the visual screening apparatus 100 that is placed facing the user desiring to test his visual acuity or for defects in his sight. The housing 10 has a first right aperture 11 and a first left aperture 21, which apertures are respectively intended to be placed facing the right eye and the left eye of the user facing in a first direction of sight. Preferably, the first direction of sight, corresponding to near vision, is inclined by about 30 degrees to a horizontal plane passing through the optical rotation center of the eyes of the user.

The visual screening apparatus 100 includes a screen 30.

The screen 30 has a first zone 31, which is placed in the interior of the housing, and which therefore does not appear in FIGS. 1-2, and a second zone 32 placed on the exterior of the housing 10. More precisely, the housing includes an opaque external wall 6 that is placed transversely to the surface of the screen so as to separate the first zone 31 from the second zone 32. The external wall 6 allows a user to access the second zone 32 for visual and/or touch interactions. In contrast, the external wall 6 prevents direct access to the first zone 31 and forms an obturator that prevents the user from viewing the first zone 31 when the screen is in place in the screening apparatus 100.

In one embodiment illustrated in FIG. 1, the screen is a flatscreen, for example an LCD screen equipped with a touch panel that is integrated into the apparatus 100. In this case, the screening apparatus includes electronics for controlling the flatscreen. In the example illustrated in FIG. 1, the screen 3 is integrated into the screening apparatus 100 and can be separated from the apparatus only by dismantling the apparatus.

Figure 3:
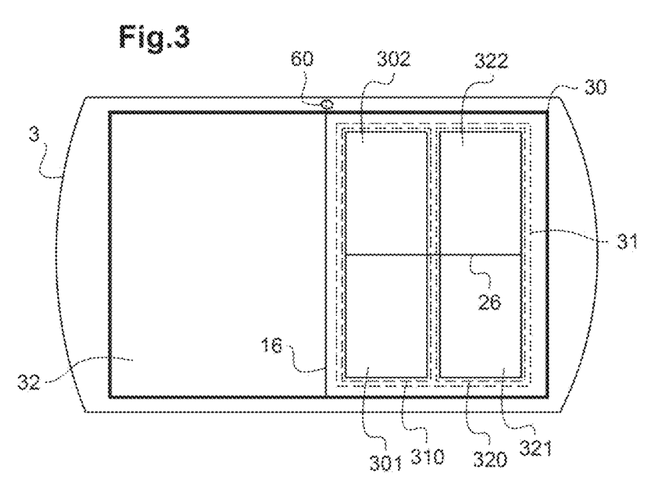
FIG. 3 shows a top view of the screen of a visual screening apparatus according to one exemplary embodiment of the invention.

In another embodiment illustrated in FIGS. 2-3, the screen is advantageously a screen of a removal touch tablet. The touch tablet 3 integrates an electrical power supply, control electronics allowing the screen to be controlled, electronics for communicating with one or more external devices of the remote control type, a controlling computer for conducting and recording the results of visual screening tests or even a printer, for the redacting of a visual screening test report.

In the example illustrated in FIG. 2, the touch tablet 3 is inserted into a slot in the apparatus and this tablet is easily removable.

In one variant, the screening apparatus includes a voice-synthesizing device configured to emit complementary explanatory audio messages depending on the visual screening tests displayed on the screen. The audio messages emitted by voice synthesis thus complement the visual messages displayed on the screen.

FIG. 3 shows a top view of the screen of a visual screening apparatus according to one exemplary embodiment of the invention.

The screen includes a first zone 31 and a second zone 32 that are spatially separate. For example, the screen is a tablet screen of 10.1 inch diagonal having a resolution of about 2560×1600 pixels, namely a resolution of 300 dpi. The first zone 31 and the second zone 32 each respectively occupy about half the area of the screen divided in the direction of its length. For example, one end of the external wall 6 of the housing of the apparatus is placed along a line 16 that separates the first zone 31 from the second zone 32.

The first zone 31 is thus placed facing an optical system in the interior of the housing of the apparatus. An exemplary optical system is described in detail in the present document with regard to FIGS. 4-5.

The first zone 31 of the screen, which zone is located in the interior of the apparatus, is configured so as to present the desired optotypes. The illumination emitted by the screen allows luminous images to be formed without an additional light source. Advantageously, the modulation of the intensity of the image emitted by the screen allows the luminance of the images to be adapted depending on the desired conditions: normal daytime illumination, illumination of low or high brightness.

Particularly advantageously, the apparatus is configured to test the vision of the user at a plurality of vision distances, for example near vision and far vision. In this case, the first zone 31 may be divided into a first portion 310 intended to display optotypes for a first vision distance, for example in near vision, and into a second portion 320 intended to display optotypes for a second vision distance, for example in far vision. Moreover, the first portion 310 may also be divided by a line 26 into a first right portion 301 of the screen, which portion is placed facing a first optical path forming an image in the direction of the right eye of the user and, respectively, a first left portion 302 of the screen, which portion is placed facing a second optical path, separate from the first optical path, forming an image in the direction of the left eye of the user. Likewise, the second portion 320 may also be divided by the line 26 into a second right portion 321 of the screen, which portion is placed facing a third optical path forming an image in the direction of the right eye of the user and, respectively, a second left portion 322 of the screen, which portion is placed facing a fourth optical path forming an image in the direction of the left eye of the user.

The external second zone 32 of the screen is thus placed in proximity to the user or patient. The second zone 32 of the screen may advantageously be used as a welcome screen allowing the one or more desired tests to be selected. This external second zone 32 provides the function of graphical and/or touch interface with the user and serves to record the responses of the patient to the screening tests.

In the case of use in a self-test mode, the external second zone 32 of the screen may serve to display a user manual or an invitation to screen his sight completely unassisted.

The screening apparatus thus has the advantage of presenting visual screening tests and of directly recording the responses of the patient on one and the same screen. The screen of the screening apparatus 100 integrates both the functions of light source and of physical support of optotypes in limitless number, and the function of interface with the user.

Figure 4:
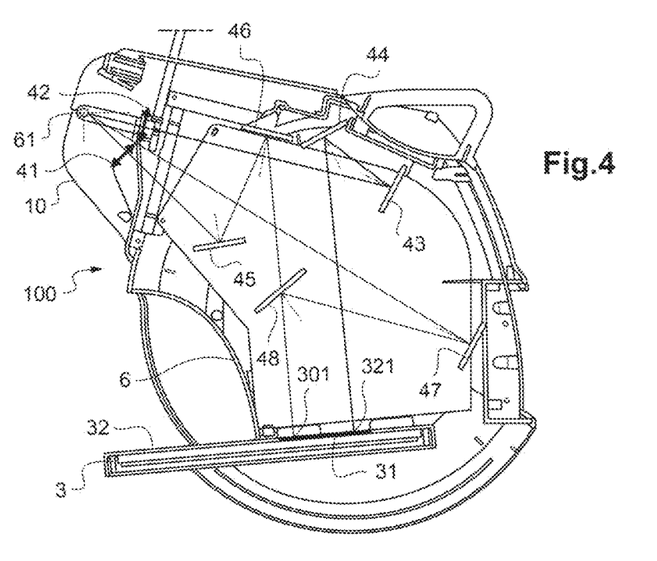
FIG. 4 shows a cross-sectional view illustrating the optoelectronic system of a visual screening apparatus according to a first variant of the invention.

FIG. 4 schematically shows a view in cross section AA of a visual screening apparatus such as shown in FIG. 2.

The screening apparatus 100 of FIG. 4 includes a housing 10 and a touch tablet 3. An external wall 6 allows the screen of the touch tablet 3 to be physically and optically separated into a first portion 31 located in the interior of the apparatus and a second portion 32 accessible from the exterior of the apparatus 100, for example to a user.

The screening apparatus 100 includes an optical system arranged so as to form an image of the first zone 31 of the screen at various vision distances depending on the direction of sight.

In the example illustrated in FIG. 4, the optical system includes lenses and mirrors.

More precisely, the optical system includes various optical paths respectively associated with various vision distances.

The user places his head against the zone 7 against which the forehead may rest and/or the chin rest 8. In this way, the right eye and left eye of the user are positioned facing the right apertures 11, 12, 13 and left apertures 21, 22, 23 of the screening apparatus 100, respectively.

Without moving his head, by simply lowering his gaze, the user inclines the direction of his gaze either toward the first right and/or left apertures 11 and/or 21 for a near-vision test, or toward the second right and/or left apertures 12 and/or 22 for a far-vision test, or toward the third right and/or left apertures 13 and/23 for a vision test at an intermediate distance.

By way of example, FIG. 4 shows the optical rotation center 61 of the right eye. For a lowering angle of the gaze comprised between 0 and 10 degrees to a horizontal plane, the axis of sight of the gaze of the user passes through the third right aperture 13 for the right eye and/or through the third left aperture 23 for the left eye, respectively. For an additional lowering angle of the gaze comprised between 10 and 15 degrees, the axis of sight of the gaze of the user passes through the second right aperture 12 for the right eye and/or through the second left aperture 22 for the left eye, respectively. Finally for yet another additional lowering angle of the gaze of about 10 to 15 degrees, the axis of sight of the gaze of the user passes through the first right aperture 11 for the right eye and/or through the first left aperture 21 for the left eye, respectively.

A first optical path is associated with near vision for the right eye and comprises a lens 41, which is placed in proximity to the first aperture 11, a planar mirror 45, a planar mirror 46 and a semitransparent plate 48. The lens 41 forms an image of a first portion 301 of the first zone 31 of the screen. One or more optotypes are displayed on the first portion 301 of the first zone 31 of the screen for a screening test in near vision. The image emitted by the first portion 301 of the screen is transmitted through the semi-reflective plate 48, reflected by the planar mirror 46 then by the planar mirror 45 and lastly transmitted by the lens 41 in the direction of the optical rotation center 61 of the right eye via the first aperture 11. The lens 41 is placed so as to form a virtual image of the first portion 301 of the screen at an optical distance smaller than or equal to 50 cm, which corresponds to the near-vision distance.

A second optical path is associated with near vision for the left eye and comprises analogous optical components that are placed symmetrically about the plane AA so as to form a virtual image of the first portion 302 of the screen in the direction of the first left aperture 21.

A third optical path is associated with far vision for the right eye and comprises a lens 42, which is placed in proximity to the second aperture 12, a planar mirror 43 and a planar mirror 44. The lens 42 forms an image of a second portion 321 of the first zone 31 of the screen. One or more optotypes are displayed on the second portion 321 of the first zone 31 of the screen for a screening test in far vision. The image emitted by the second portion 321 of the screen is reflected by the planar mirror 44 then by the planar mirror 43 and lastly transmitted by the lens 42 in the direction of the optical rotation center 61 of the right eye via the second aperture 12, which is located facing the right eye on the far sight axis. The lens 42 is placed so as to form a virtual image of the second portion 321 of the screen at an optical distance larger than or equal to 4 meters, which corresponds to the far-vision distance.

A fourth optical path is associated with far vision for the left eye and comprises analogous optical components (aperture 22, lens 42, mirrors 43, 44) that are placed symmetrically about the plane AA so as to form a virtual image of the second portion 322 of the screen in the direction of the second left aperture 22.

Advantageously, fifth and sixth optical paths associated with intermediate vision comprise a planar mirror 47 and the semi-reflective plate 48. One or more optotypes are displayed on the first portion 301 of the first zone 31 of the screen for a screening test in intermediate vision. The image emitted by the first portion 310 of the screen is reflected from the semi-reflective plate 48, then from the planar mirror 47. Thus, the fifth optical path forms the image of the first portion 301 of the screen via the third right aperture 13 on the right eye and the sixth optical path forms the image of the first portion 302 of the screen via the third left aperture 23 on the left eye, respectively. The fifth and sixth optical paths pass for example between the lenses 41 and 43. The fifth or sixth optical path allows the eye of the user to form an image of the first portion 301, 302 of the screen at an optical distance comprised between 50 cm and 3 meters, which corresponds to the intermediate-vision distance.

The optical system of the visual screening apparatus is fixed: no optical component need be moved to modify the direction of sight of the gaze nor the vision distance of the optotype images. The position of the screen thus remains fixed and independent of the optical proximity of the tests for the various proximity values. This optical configuration makes the visual screening apparatus very robust.

The redirecting planar mirrors 43, 44, 45, 46, 47 and the semi-reflective plate 48 allow the various optical paths to be folded so as to make the screening apparatus very compact.

The semi-reflective plate 48 allows, in a passive way, the same portion 310 of the first zone of the screen to be used to form optotype images at two distinct vision distances and in two distinct directions of sight of the gaze. A movable obturator (not shown) allows an optical path corresponding to one or other of the two vision distances to be selected.

In an embodiment such as detailed above, the optical system includes a right optical path such as detailed above and a left optical path, which is symmetric with the right optical path about the plane of FIG. 4, in order to form various optical channels between, on the one hand, the first, second and third left apertures 21, 22 and 23 and, on the other hand, the first left portion 302 and the second left portion 322 of the screen. The lenses 41, 42 used are preferably distinct optical components on the right and left optical paths. The mirrors 43-47 and the semi-transparent plate used on the right and left optical paths may either be distinct components or consist of components extending on either side of the plane of symmetry AA.

In another embodiment, the same optical components simultaneously allow various optical channels to be formed between, on the one hand, the first, second and third left apertures 21, 22 and 23, and, on the other hand, the first portion of the screen 31, and more precisely the first left portion 302 and the second left portion 322 of the screen.

By simply lowering his gaze, the user may view optotype images in directions of sight corresponding to the natural lowering angle of the gaze in near vision, far vision and intermediate vision, respectively, and at respective distances corresponding to the distances for example indicated in standard ISO8596.

Preferably, the apparatus includes means for optically isolating the right optical channel from the left optical channel at the various vision distances. The optical isolating means for example comprise an opaque internal partition in a vertical plane of symmetry (for example the cross-sectional plane AA in FIG. 2) of the screening apparatus 100. This internal partition allows parasitic internal reflections to be prevented. The optical isolating means may also comprise diaphragms placed in proximity to one or more mirrors 43-47.

Alternatively and/or in addition, the screening apparatus includes one or more obturators allowing one or more of the apertures 11, 12, 13, 21, 22, 23 to be selectively obturated. These obturators allow the extent of the field of view to be limited in a given direction of sight.

For a test in monocular vision, the selective display capacities of the screen are used to form an image on a predetermined portion of the screen 301, 302, or 321, 322.

Particularly advantageously, the optical system includes convergence prisms placed in front of the right and left apertures in particular in order to compensate for the convergence of the gaze in near vision and/or in intermediate vision. The screen 31 and the optical system form an image for each eye at a determined vision distance. The convergence prisms allow the two eyes to converge at the presentation distance. Thus, the user may fuse the two, right and left, images at the chosen vision distance.

Figure 5:
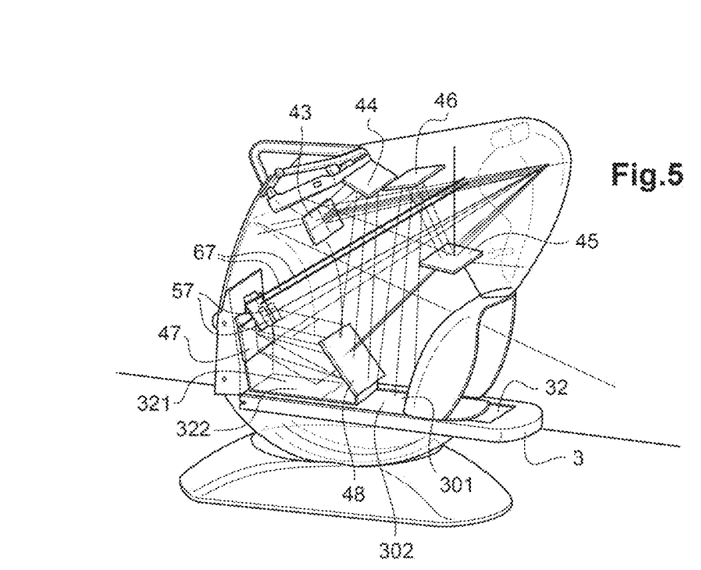
FIG. 5 shows an internal perspective view illustrating the optical paths in a visual screening apparatus according to another variant of the invention.

FIG. 5 schematically shows the various optical paths according to one variant of a visual screening apparatus.

The same elements are designated by the same reference numbers as in FIG. 4.

In the variant in FIG. 5, the first and second optical paths corresponding to near vision start from the first right and left portion of the screen, 301 and 302 respectively, are reflected from the planar mirror 46 and from the planar mirror 45 and then are transmitted in the direction of sight corresponding to a lowering of the gaze of about 30 degrees. The third and fourth optical paths corresponding to far vision start from the second right and left portion of the screen, 321 and 322 respectively, are transmitted by the semi-reflective plate 48, are reflected from the planar mirror 44 and from the planar mirror 43 and then are transmitted in the direction of sight corresponding to a lowering of the gaze of about 15 degrees. Finally, the fifth and sixth optical paths corresponding to intermediate vision start from the second right or left portion 321 or 322 of the screen, are reflected by the semi-reflective plate 48 and then from the planar mirror 47 in the direction of sight corresponding to a lowering of the gaze of about 25 degrees. Thus, in this variant, the semi-reflective plate 48 separates the far-vision and intermediate-vision optical paths. For comparison, in the embodiment illustrated in FIG. 4, the semi-reflective plate 48 separates the near-vision and intermediate-vision optical paths.

The dimensions of the mirrors are selected depending on their position in order to allow the user to experience a comfortable field of view along the optical path of each eye and for each axis of sight of the gaze.

Optionally, the screening apparatus in FIG. 5 furthermore includes a subassembly for measuring the reserve accommodation of the patient, also called the punctum proximum. As is moreover known, a measurement of reserve accommodation is intended to determine the reserve accommodation of the user, i.e. his least distance of distinct vision. This measurement especially allows incipient presbyopia to be screened for.

In the example shown in FIG. 5, the subassembly for measuring reserve accommodation includes two, right and left, test holders 57 that are translatably movable along guiding rails 67 placed parallel to the intermediate-vision axis. A coded motorization for example allows the optical distance between the test holders 57 and the user in the intermediate-sight direction to be modified. Advantageously, the test holder 57 is illuminated by the illuminating system of the screen and for example backlit. Preferably, the subassembly for measuring reserve accommodation is mounted on a retracting device that is combined with the translational movement so as to make it possible to free the field of view when this subsystem is not being used. For example, the retracting device includes two pinions located on either side of the translational axis of the subassembly. When the subassembly arrives at the end of travel of the translational movement, the two pinions engage in two racks placed directly opposite. A rotational movement of the two test holders 57 occurs until the final retraction of the test holders 57.

The reduction in the luminosity of the image emitted by the screen, which is optionally associated with a filter, may be used to evaluate visual acuity under mesopic vision conditions, i.e. of very low ambient lighting.

In one embodiment (not illustrated in the figures), a third zone of the screen 30 is accessible to and visible by an operator, but not by the user. For example, the third zone of the screen is placed opposite the first zone of the screen, which first zone is placed facing the user. In one exemplary embodiment, the first zone is accessible from the exterior of the housing, on one side of the screening apparatus, and the third zone of the screen 30 is accessible from the exterior of the housing on the opposite side of the screening apparatus, the second zone remaining inaccessible and hidden from view in the interior of the housing. This third zone allows an operator or an optician to control the progression of a sequence of screening tests and/or to follow the progression of the tests of a user.

The screening apparatus may be available in a basic version with only a touchscreen autonomously accessible to the user and in a more complete version with a voice synthesizing device for assisting the user in the self-tests.

Use of the screening apparatus may also require the intervention of an operator having access to a zone of the screen that is not accessible to the user, or having access to an interface connected to the screening apparatus by wired or wireless telecommunications means, this interface for example comprising a control computer the screen of which duplicates the first zone of the screen of the screening apparatus and control buttons.

Various options may be integrated into the screening apparatus with a view to performing tests other than visual acuity tests or to modifying the conditions under which the visual acuity tests are carried out.

As indicated above, the light emitted by the screen is enough to form a test image, in a luminance range corresponding to daytime illumination.

Optionally, the screening apparatus includes additional elements for example for carrying out a glare test, a contrast sensitivity test, or a measurement of mesopic visual acuity.

To carry out a glare test, the apparatus integrates an additional light source placed in the field of view of the user when the latter is looking through one of the apertures. The additional light source is selected so as to emit a luminance for about ten seconds in order to dazzle the patient and generate a scotoma of sufficient size for the test in question. This device thus allows the recuperation of the visual function of the user after he has been dazzled to be analyzed.

To carry out a contrast sensitivity test, with the screening apparatus the visual acuity of the patient under standard luminance conditions is measured with black optotypes on a white background, said optotypes being displayed with the maximum possible contrast depending on specificities of the screen used. Next, the level of contrast of the optotypes is modified, for example by reducing the contrast of the optotypes from 1 to 0.1. It is thus possible to measure visual acuity as a function of contrast and in particular at low contrasts.

This test allows a decrease in visual acuity under conditions of low levels of contrast, which is especially observed on the appearance of a cataract or other diseases of the eye, to be screened for. This device allows a decrease in visual-acuity performance to be identified.

Moreover, the aim of a mesopic-vision visual-acuity measurement is to quantify the loss of visual acuity as a function of the illumination level. The screening apparatus advantageously includes computational means for automatically adjusting the level of luminance, the level of contrast of the optotypes and the color of the background of the screen. To carry out the mesopic-vision visual-acuity measurement, the optotypes are presented and the level of luminance and of contrast of the background of the image displayed by the screen is varied, starting under photopic vision conditions, with a luminance of at least 100 $cd/m^2$ and, by means of an optical density, then decreasing the luminance until mesopic-vision conditions, with a luminance lower than about 10 $cd/m^2$, and preferably of about 2 $cd/m^2$, are obtained. Preferably, the optotypes are modified by acting on two parameters conjointly: modification of the luminance of the screen (for example in a backlit screen), and modification of the contrast of the displayed optotypes relative to the background of the screen, for example by modifying the background color. The modification of these two parameters allows the dynamic range of the luminance of the screen to be increased.

To allow a sufficient luminance to be obtained in the various directions of sight, on account of the presence of the semi-reflective plate on the optical path between the intermediate channel and the near-vision or far-vision channel, it is preferable to select a screen having a luminance at least equal to two-times the luminance of at least 100 $cd/m^2$ and to adjust the luminance of the screen depending on the optical path. Thus, the user perceives images having a mean luminance substantially identical whatever the direction of sight.

The tablet generally comprises a battery or means for connecting to a source of electrical current.

The screening apparatus 100 has the advantage of having a very low power consumption because the screen of the tablet is the main source of power consumption, the opto-mechanical system of mirrors and lenses remaining fixed and entirely passive.

The screen is easily interchangeable for updating of the hardware or software of the apparatus.

Method

FIG. 3 shows a top view of a screen 30 of a touch tablet 3 integrated into an apparatus for screening for defects in the sight of a user.

The screening apparatus 100 incorporates a flat LCD screen equipped with a touch panel. This screen is implanted into an apparatus so that a first zone of the surface of the screen is directly opposite optical channels in the interior of the screening apparatus and so that the second zone 32 of the screen may be seen from the exterior of the screening apparatus, this second zone 32 being placed in proximity to the patient.

The functions of the screen are advantageously provided by a touch tablet, the control electronics of the tablet being used to control the screen and the communication with other electronic systems such as a remote control or a computer or printer for redacting and saving a screening test report.

Complementarily, audio functions may be provided for explanatory purposes. Optionally, the screening apparatus furthermore allows hearing to be screened.

The first zone 31 of the screen is not accessible to the user and is electronically and computationally controlled so as to present the desired optotypes.

The second zone 32 of the screen is accessible for the display of information and to record the responses of the user by tactile interaction, during the tests. The external second zone 32 may be used as a welcome screen allowing the one or more desired tests to be selected by the user. The second zone 32 of the screen provides the functions of a human-machine interface between the user and the screening apparatus. For example, in the case of use in a self-test mode, the external second zone 32 may display a user manual or an invitation to screen his sight completely unassisted.

Optionally, a third zone of the screen, which zone is also placed on the exterior of the housing of the screening apparatus, allows a duplication of the optotype presented on the first zone to be simultaneously displayed. This third zone is advantageously placed facing an operator or a medic in order to allow him to follow in real-time the progression of the screening examination.

The user validates the initiation of a screening test, for example, by a click on a touch button in the second zone 32 of the screen. Next, he places his head in abutment against the chin rest 8 and/or the forehead rest. Thus, his right eye is facing a right aperture of the housing of the apparatus and his left eye faces a left aperture.

For a screening test in stereoscopic vision, the right image and the left image are activated, whereas for a screening test in monocular vision, a single, right or left, image is activated, the rest of the screen remaining black.

The electronic and computational system of the apparatus is configured to display on the first zone 31 of the screen tests at a predetermined proximity or distance (preferably corresponding to near, far and/or intermediate vision) and to directly record the responses of the patient via the external second zone 32 of the screen.

Figure 6A:
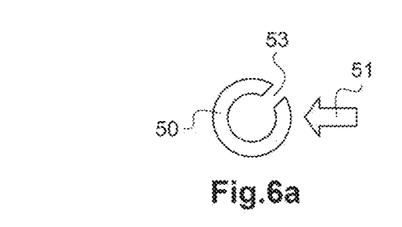
FIG. 6 illustrates a graphic interface for indicating the position of the aperture of a Landolt ring according to one embodiment of the method of the invention.
Figure 6B:
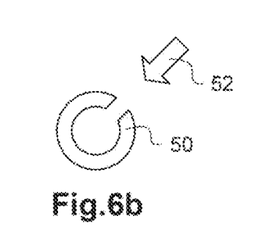

FIGS. 6A-6B illustrate an exemplary graphical interface for a test based on Landolt rings.

Automatically or following a touch interaction of the user in the second zone 32, a Landolt ring 50 is displayed in the first zone 31 of the screen, for example in the first right portion 301. The Landolt ring 50 is displayed in a dark color on a light background, and preferably in black on a white background. The control software or the user adjusts the diameter of the Landolt ring to test the user's visual acuity for a determined size of the optotype and for a determined vision distance. The Landolt ring 50 includes an aperture 53. The software generates a Landolt ring of determined diameter, but the orientation of the aperture of which is randomly selected from eight orientations: 0, +45, +90, +135, +180, +225, +270 and +315 degrees relative to a vertical line. In the example in FIG. 6, the orientation of the Landolt ring is +45 degrees.

The aim of the test is to determine whether the user has a visual acuity allowing him to correctly distinguish the orientation of the Landolt ring.

The method may provide various variant ways of recording the response of the user via the second zone 32 of the touchscreen.

According to a first variant, illustrated in FIGS. 6A and 6B, firstly a Landolt ring is displayed, then, when the user presses on the zone 32, an arrow (or another suitable graphical indicator) is displayed in an initial position 51 that is independent of the orientation of the Landolt ring 50.

The user looks, via the selected aperture and along the appropriate axis of sight, at the image displayed in the first zone of the screen, which allows him to simultaneously observe the Landolt ring and the arrow.

By slide-movement actions on the external zone 32, the user is able to move the arrow around the Landolt ring, preferably in steps of ⅛ of a revolution. When the user considers visually in the displayed image that the arrow is placed so as to indicate the orientation of the aperture of the ring, he validates the position of the arrow 53, for example via a touch button on the second zone 32 of the screen. The computational system thus records the response of the user and analyses whether this response is correct or not.

The system may carry out a series of a plurality of tests for a given diameter and various orientations of the Landolt ring.

Depending on the recorded responses, the control system modifies the diameter of the displayed Landolt ring in order to pass to a higher or lower degree of the visual-acuity scale.

In another variant, two Landolt rings of the same diameter are displayed in superposition. The first Landolt ring has a fixed orientation chosen randomly from the eight orientations. In contrast, the second Landolt ring has an orientation that varies depending on interactions of the user in the second zone: by interactions with the touch panel in the second zone 32 of the touchscreen, the user may make the second Landolt ring turn about itself in one direction or the other whereas the first Landolt ring remains stationary. When the orientation of the two Landolt rings is different one from the other, the screen displays a complete circle, the aperture of each Landolt ring being obturated by the circle of the other Landolt ring, respectively. When the orientation of the second Landolt ring coincides with the orientation of the first Landolt ring, the screen displays a Landolt ring having the orientation of the first ring. When the user considers visually in the displayed image that he is able to see the image of an open Landolt ring and not of a closed circle, he validates the orientation of the second ring, for example via a click on a touch button of the second zone 32 of the screen.

The electronic and computational system then records the response of the user.

These two variant methods for determining the orientation of a Landolt ring are essentially based on a graphical display and on a touch input. These two variants allow false positives associated with the determination of the orientation of a Landolt ring based on an oral or written response of the user to be avoided.

However, the screening system and method are in no way limited to the use of Landolt rings. They are also compatible with visual screening tests based on the recognition of alphanumeric characters, such as illustrated in FIG. 7.

Figure 7:
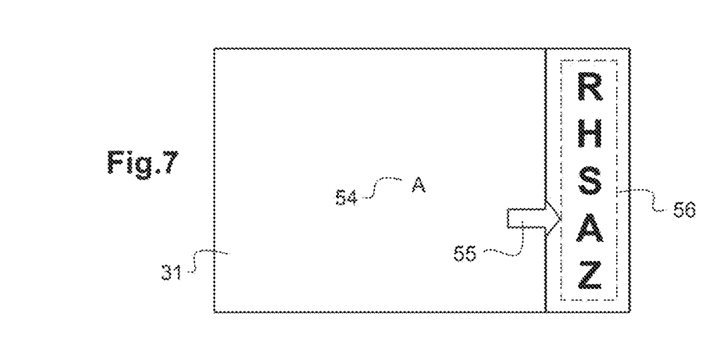
FIG. 7 illustrates a graphic interface for indicating a displayed alphanumeric symbol according to another embodiment of the method of the invention.

FIG. 7 shows a graphical interface displaying an alphanumeric symbol 54 randomly selected by the computational system from a plurality of alphanumeric symbols.

In a first step, a letter 54 is displayed on the screen. In a second step, for example in the right-hand portion of the image, a table 56, which contains a set of alphanumeric symbols, one of which is identical to that displayed in the left-hand portion of the screen 31, is displayed.

An arrow 55, or any other suitable graphical indicator, is simultaneously displayed in proximity to the table 56 of alphanumeric symbols. By interactions in the second zone 32 of the screen, for example via top-to-bottom slide-movement actions, the user may move the position of the arrow 55 in the displayed image, so as to place the arrow 55 facing one or other of the alphanumeric symbols of the series 56. When the user considers visually in the displayed image that the arrow 55 indicates the same alphanumeric symbol in the series 56 as at the center of the image, he validates the position of the arrow, for example via a click on a touch button of the second zone 32 of the screen.

The user may thus record, via touch interactions in the second zone of the screen 32, his responses to a visual test displayed in the first zone of the screen, without needing to give responses involving oral or written language, thereby allowing him to avoid communication errors.

Other screening tests may be implemented in the screening apparatus, such as a test of astigmatism (astigmatic mirror test) displaying radii of a semicircular arc and in which a graphical cursor, for example circular bars at the end of the radii, allow the radius perceived by the patient as being the most contrasted to be identified. The patient records his response by means of the touch panel in an analogous way to one of the embodiments described above.

The tests may be carried out in monocular vision on each eye separately. Other tests may be carried out in stereoscopic vision, each eye viewing a different virtual image formed along a separate optical path and the patient fusing, or not, the right virtual image with the left virtual image.

The screening method thus allows various visual screening tests to be taken, in particular:

measurement of reserve accommodation or punctum proximum;
glare test;
measurement of visual acuity with a Landolt-ring scale or alphanumeric-character scale;
measurement of contrast sensitivity;
measurement of visual acuity in mesopic vision;
astigmatism test;
hypermetropic tendency;
ametropic tendency;
color vision;
depth perception.

The invention claimed is:

1. A bi-ocular optoelectronic apparatus for screening for defects in the sight of and for measuring the visual acuity of a user, the bi-ocular optoelectronic apparatus comprising:

a housing having a first right aperture and a first left aperture, the first right aperture and the first left aperture being respectively intended to be placed facing the right eye and the left eye of the user facing in a first direction of sight, the housing having an opaque external wall;

a touchscreen comprising a first zone and a second zone that are spatially separate, the opaque external wall being disposed transversely to a surface of the touchscreen to physically and optically separate the first zone from the second zone, the touchscreen being placed in the bi-ocular optoelectronic apparatus so that the first zone of the touchscreen is in the interior of the housing and so that the second zone of the touchscreen is accessible from the exterior of the housing;

control electronics configured to display a plurality of optotypes in a first portion of the first zone of the touchscreen, internal to the housing; and an optical system placed in the interior of the housing, the optical system being configured to form a first right image of the first portion of the first zone of the touchscreen in the direction of the first right aperture at a first vision distance following a first optical path, and the optical system being configured to form a first left image of the first portion of the first zone of the touchscreen in the direction of the first left aperture at said first vision distance following a second optical path.

2. The bi-ocular optoelectronic apparatus for screening for defects in the sight of and for measuring the visual acuity of a user as claimed in claim 1, wherein the second zone of the touchscreen is configured to record touch interactions of the user, and the bi-ocular optoelectronic apparatus further comprising a control system configured to modify the display of said optotypes in the first portion of the first zone of the screen depending on the recorded touch interactions and/or to record a response of the user to a viewed first right image and/or to a viewed first left image depending on said recorded touch interactions.

3. The bi-ocular optoelectronic apparatus for screening for defects in the sight of and for measuring the visual acuity of a user as claimed in claim 1, wherein the housing further comprises a second right aperture and a second left aperture, the second right aperture and the second left aperture being respectively intended to be placed facing the right eye and the left eye of the user facing in a second direction of sight, the control electronics is configured to display a plurality of optotypes in a second portion of the first zone of the touchscreen, internal to the housing, and the optical system is configured to form a second right image of the second portion of the first zone of the touchscreen in the direction of the second right aperture at a second vision distance following a third optical path, and the optical system is configured to form a second left image of the second portion of the first zone of the touchscreen in the direction of the second left aperture at said second vision distance following a fourth optical path.

4. The bi-ocular optoelectronic apparatus for screening for defects in the sight of and for measuring the visual acuity of a user as claimed in claim 3, wherein the housing further comprises a third right aperture and a third left aperture, the third right aperture and the third left aperture being respectively intended to be placed facing the right eye and the left eye of the user facing in a third direction of sight, and the optical system being configured to form a third right image of a portion of the first zone of the touchscreen in the direction of the third right aperture at a third vision distance following a fifth optical path, and the optical system is configured to form a third left image of the third portion of the first zone of the touchscreen in the direction of the third left aperture at said third vision distance following a sixth optical path.

5. The bi-ocular optoelectronic apparatus for screening for defects in the sight of and for measuring the visual acuity of a user as claimed in claim 1, further comprising a speech synthesizer.

6. The bi-ocular optoelectronic apparatus for screening for defects in the sight of and for measuring the visual acuity of a user as claimed in claim 1, wherein the touchscreen is placed in the bi-ocular optoelectronic apparatus to have an external third zone configured to serve as an operator interface, said external third zone being spatially separate from said first zone and second zone of the touchscreen.

7. The bi-ocular optoelectronic apparatus for screening for defects in the sight of and for measuring the visual acuity of a user as claimed in claim 1, further comprising one or more obturators configured to obture the first right aperture and/or the first left aperture.

8. The bi-ocular optoelectronic apparatus for screening for defects in the sight of and for measuring the visual acuity of a user as claimed in claim 2, wherein the plurality of optotypes includes a Landolt ring having a determined orientation and diameter, and wherein the control system is configured to indicate the orientation or to modify the orientation and/or the diameter of the Landolt ring by interaction of the user via the external second zone of the touchscreen.

9. The bi-ocular optoelectronic apparatus for screening for defects in the sight of and for measuring the visual acuity of a user as claimed in claim 2, wherein the plurality of optotypes includes an alphanumeric character having a determined size, and wherein the control system is configured to designate an alphanumeric character from a set (56) of alphanumeric characters or for modifying the displayed alphanumeric character and/or the size of the displayed alphanumeric character by interaction of the user via the external second zone of the touchscreen.

10. The bi-ocular optoelectronic apparatus for screening for defects in the sight of and for measuring the visual acuity of a user as claimed in claim 2, wherein the control system is configured to deduce from the recording a measurement of the visual acuity of the right eye and/or of the left eye for the first vision distance, for the second vision distance and/or for the third vision distance, respectively, the first vision distance preferably corresponding to a near-vision distance smaller than or equal to 50 cm, the second vision distance preferably corresponding to a far-vision distance larger than or equal to 4 meters and the third vision distance preferably corresponding to an intermediate-vision distance comprised between 50 cm and 3 m.

11. The bi-ocular optoelectronic apparatus for screening for defects in the sight of and for measuring the visual acuity of a user as claimed in claim 1, wherein the control electronics are configured to the luminance and/or contrast of the images displayed in the first zone of the touchscreen.

12. The bi-ocular optoelectronic apparatus for screening for defects in the sight of and for measuring the visual acuity of a user as claimed in claim 1, further comprising a subassembly configured to measure a reserve accommodation of the user.

13. The bi-ocular optoelectronic apparatus for screening for defects in the sight of and for measuring the visual acuity of a user as claimed in claim 11, wherein the first zone of the touchscreen, internal to the housing, is configured to form an illuminating system configured to illuminate an optotype to measure a reserve accommodation of the user.

14. The bi-ocular optoelectronic apparatus for screening for defects in the sight of and for measuring the visual acuity of a user as claimed in claim 1, wherein the touchscreen is removable from the housing of the apparatus.

15. A method for screening for defects in the sight of and for measuring the visual acuity of a user, the method implementing the bi-ocular optoelectronic apparatus as claimed in claim 1 and comprising:

displaying a plurality of optotypes in the first zone of the touchscreen, said plurality of optotypes comprising at least one Landolt ring, having a diameter and an aperture of predetermined orientation;

modifying the diameter and/or a visually detected indication of the orientation of the aperture of the Landolt ring by interaction via the second zone of the touchscreen; and validating, via the second zone of the touchscreen, a diameter and/or a visually detected indication of the orientation of the Landolt ring, the validation being by the user.

16. A method for screening for defects in the sight of and for measuring the visual acuity of a user, the method implementing the bi-ocular optoelectronic apparatus as claimed in claim 1 and comprising:

displaying a plurality of optotypes in the first zone of the touchscreen, said plurality of optotypes comprising at least one alphanumeric character, having a predetermined size;

modifying the displayed alphanumeric character, the size of the displayed alphanumeric character and/or an indication of the alphanumeric character by interaction via the second zone of the touchscreen; and validating, via the second zone of the touchscreen, a size and/or an indication of the displayed alphanumeric character, the validation being by the user.

17. The bi-ocular optoelectronic apparatus for screening for defects in the sight of and for measuring the visual acuity of a user as claimed in claim 3, further comprising one or more obturators configured to obture the second right aperture and/or the second left aperture.

18. The bi-ocular optoelectronic apparatus for screening for defects in the sight of and for measuring the visual acuity of a user as claimed in claim 4, further comprising one or more obturators configured to obture the third right aperture and/or the third left aperture.

19. The bi-ocular optoelectronic apparatus for screening for defects in the sight of and for measuring the visual acuity of a user as claimed in claim 2, wherein the housing further comprises a second right aperture and a second left aperture, the second right aperture and the second left aperture being respectively intended to be placed facing the right eye and the left eye of the user facing in a second direction of sight, the control electronics is configured to display a plurality of optotypes in a second portion of the first zone of the touchscreen, internal to the housing, and the optical system is configured to form a second right image of the second portion of the first zone of the touchscreen in the direction of the second right aperture at a second vision distance following a third optical path, and the optical system is configured to form a second left image of the second portion of the first zone of the touchscreen in the direction of the second left aperture at said second vision distance following a fourth optical path.

20. The bi-ocular optoelectronic apparatus for screening for defects in the sight of and for measuring the visual acuity of a user as claimed in claim 2, further comprising a speech synthesizer.

\* \* \* \* \*